United States Patent [19]

Toone

[11] Patent Number: 4,901,737
[45] Date of Patent: Feb. 20, 1990

[54] METHOD AND THERAPEUTIC APPARATUS FOR REDUCING SNORING

[76] Inventor: Kent J. Toone, 1551 Elka Ave., San Jose, Calif. 95129

[21] Appl. No.: 37,609

[22] Filed: Apr. 13, 1987

[51] Int. Cl.$^4$ .................................................. A61P 5/56
[52] U.S. Cl. .................................... 128/848; 128/859; 128/861
[58] Field of Search ................ 128/136, 137, 846–848, 128/12, 859, 172.1, 860, 861, 862

[56] References Cited

U.S. PATENT DOCUMENTS

| | | | |
|---|---|---|---|
| 1,401,646 | 12/1921 | Ronn | 433/93 |
| 1,498,219 | 7/1924 | Williams | 128/12 |
| 1,556,493 | 11/1925 | Conway | 128/137 |
| 2,590,118 | 3/1952 | Oddo, Jr. | 128/136 |
| 2,630,117 | 3/1953 | Coleman | 128/136 |
| 2,844,142 | 7/1958 | Gibbons | 128/12 |
| 2,966,908 | 1/1961 | Cathcart et al. | 128/136 |
| 3,217,708 | 11/1965 | Roberts | 128/136 |
| 3,277,892 | 10/1966 | Tepper | 128/419 R |
| 3,434,470 | 5/1966 | Strickland | 128/848 |
| 4,553,549 | 11/1985 | Pope et al. | 128/421 |
| 4,715,368 | 12/1987 | George | 128/136 |

OTHER PUBLICATIONS

Weitzman E. D., et al., Quantitative Analysis of Sleep and Sleep Apnea Before and After Tracheostomy in Patients with the Hypersomnia—Sleep Apnea Syndrome, Sleep, vol. 3, No. 314, pp. 407–423 (1980).
Harman, E. M. et al., The Effect of Weight Loss on Sleep-Disordered Breathing and Oxygen Desaturation in Morbidly Obese Man, Chest, vol. 82, No. 3, pp. 291–294 (Sep. 1982).
Conway, W. A. et al., Adverse Effects of Tracheostomy for Sleep Apnes, JAMA, vol. 246, No. 4, pp. 347–350 (Jul. 24/31, 1981).
Fujita, S., et al., Surgical Correction of Anatomic Abnormalities in Obstructive Sleep Apnea Syndrome: Uvulopalatopharygoplasty, Otolaryngol Head Neck Surg., vol. 89, pp. 923–934 (Nov./Dec. 1981).
Sullivan, C. E. et al., Reversal of Obstructive Sleep Apnea by Continuous Positive Airway Pressure Applied Through the Nares, The Lancet, Apr. 18, 1981, pp. 862–865.
Mahadevia, A. K. et al., Effects of Expiratory Positive Airway Pressure on Sleep-Induced Respiratory Abnormalities in Patients with Hypersomnia–Sleep Apnea Syndrome, Am Rev Respir Dis 1983, vol. 128, pp. 708–711.
Soll, B. A. and George, P. T., Treatment of Obstructive Sleep Apnea with a Nocturnal Airway–Patency Appliance, vol. 313, No. 6, Aug. 8, 1985, pp. 386–387.

(List continued on next page.)

Primary Examiner—Mickey Yu
Assistant Examiner—Michael Brown
Attorney, Agent, or Firm—Jacques M. Dulin

[57] ABSTRACT

A non-surgical, non-invasive therapeutic apparatus and method, of an adult oral cavity appliance that improves airway patency for correcting snoring and/or obstructive sleep apnea due to intermittent closures or partial obstructions occurring in the oro pharynx. The appliance repositions the mandible in an inferior (open) and anterior (protrusive) position as compared to the normal closed position of the jaw, typically, on the order to 10–20 mm inferior, and 3–10 mm (preferably 3–6 mm) anterior. It is a rigid, generally V-shaped wedge molded to the entire mandibular dentition and a portion of the maxillary dentition. It is completely open in the front, and preferably open at the top (across the palatal arch). The mandibular incisal edge is embedded, with a lip extending about 1–2 mm over the labial surface of the mandibular incisors. It extends over the lingual surfaces of all mandibular teeth and downwardly into the lingual vestibule. It covers the palatal surfaces of the maxillary bicuspids and molars and extends onto the palate. The lack of full palatal coverage provides space for the tongue, which rests in its normal position. Results indicate reduction in snoring and related apneic episodes, and the device can be worn for full sleep periods without discomfort.

12 Claims, 3 Drawing Sheets

OTHER PUBLICATIONS

Salzman, J. A., Practice of Orthodontics, Philadelphia J. B. Lippincott, 1966.

Cartwright, R. D. et al., The Effects of a Non-Surgical Treatment for Obstructive Sleep Apnea, JAMA, vol. 248, No. 6, pp. 705–709, Aug. 13, 1982.

Coleman, R. M. et al., Sleep-Wake Disorders Based on a Polysomnographic Diagnosis, JAMA, vol. 247, No. 7, pp. 997–1003, Feb. 19, 1982.

Stalking a Good Night's Sleep, Consumer Reports, Mar. 1987, pp. 136–138.

Haze, J. J., Overview of Sleep Disorders and The Implication on Dental Practice, The Functional Orthodontist, Sep./Oct. 1987, pp. 15–18.

Device Heads Off Disorder During Sleep, INSIGHT, Aug. 10, 1987, p. 61.

Journal of the California Dental Association, Oct. 1988, pp. 2, 3, 5, 12–16, 19–24, 26–33, 35–39.

George, P., A Modified Functional Appliance for Treatment of Obstructive Sleep Apnea, J. Clinical Orthodontics, vol. XXI, No. 31, 3/87, pp. 171–175.

Graber, T. M. and Neumann, B., Removable Orthodontic Appliances, W. B. Saunders Co., (1977), Ch. 9, The Bionator, pp. 229–246.

Device Head Off Disorder During Sleep, Insight (magazine), Aug. 10, 1987, p. 61, under byline of Dina van Pelt (discussing EQUALIZER).

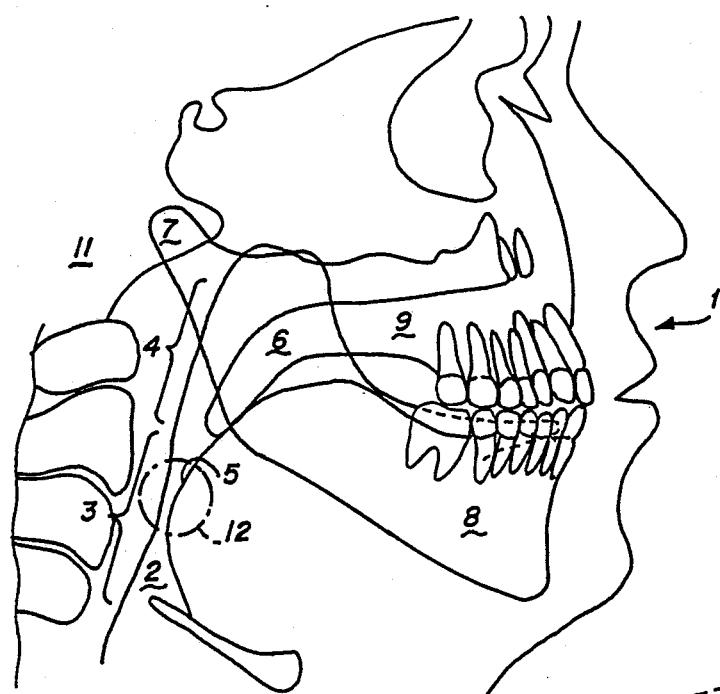
Fig_1
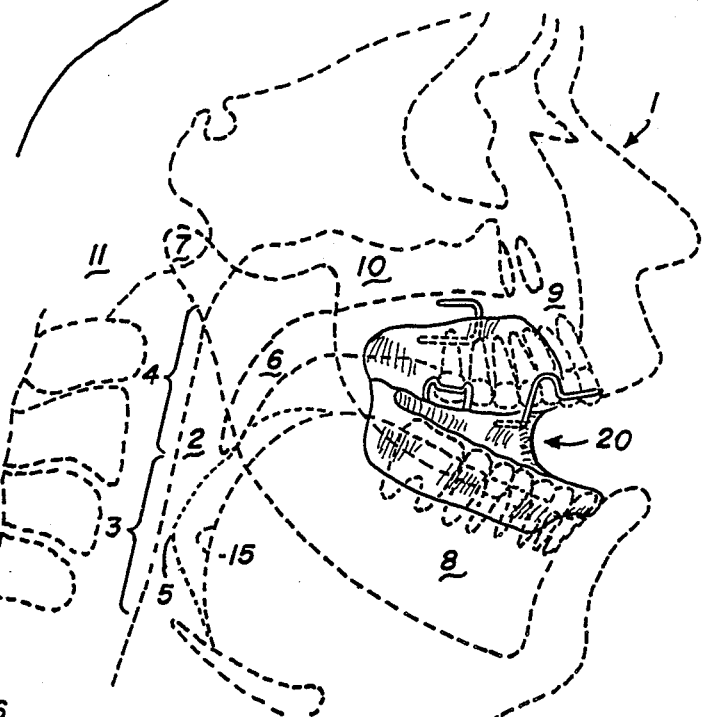
Fig_2
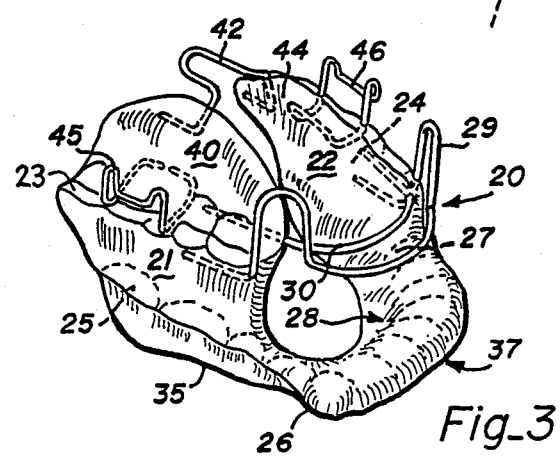
Fig_3

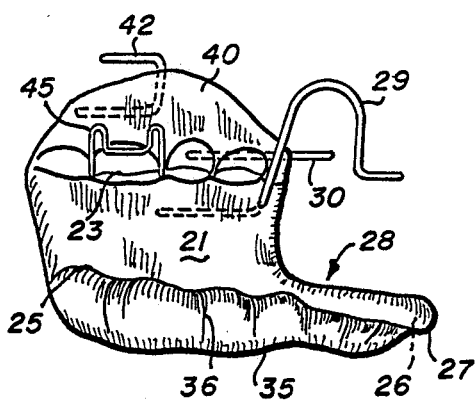
Fig_4
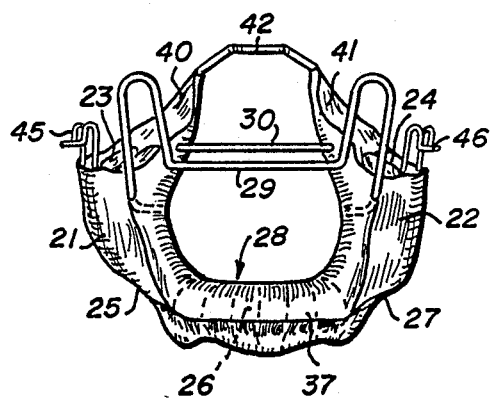
Fig_5
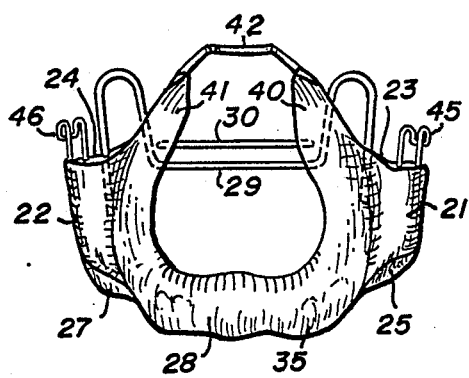
Fig_6
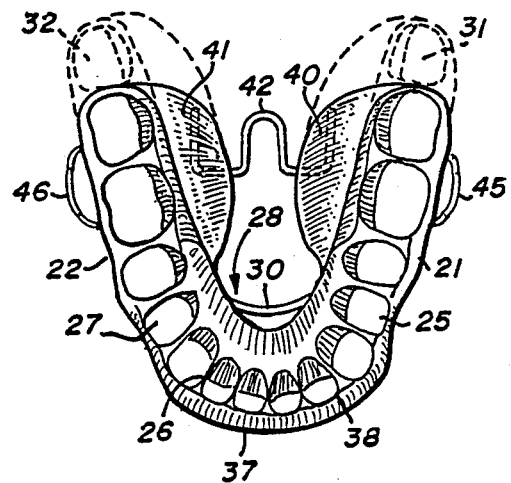
Fig_7
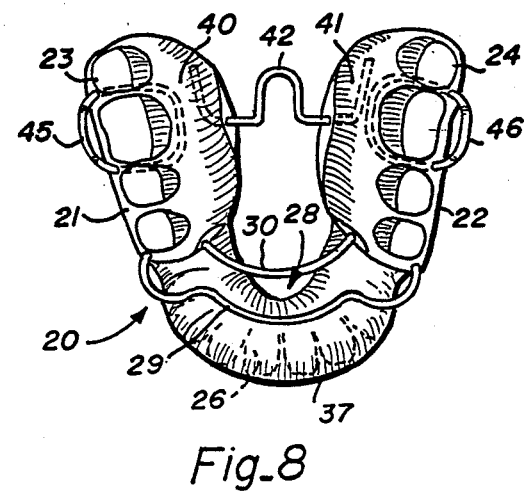
Fig_8

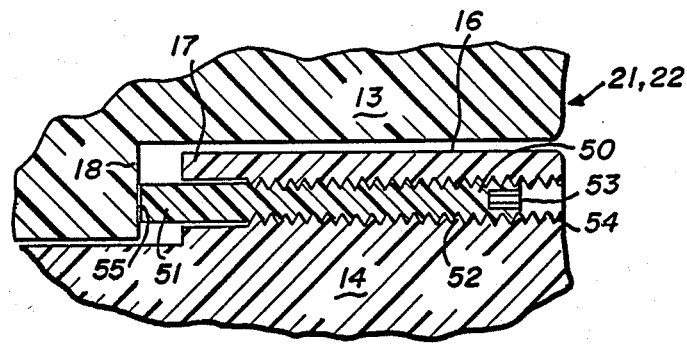
Fig_9a
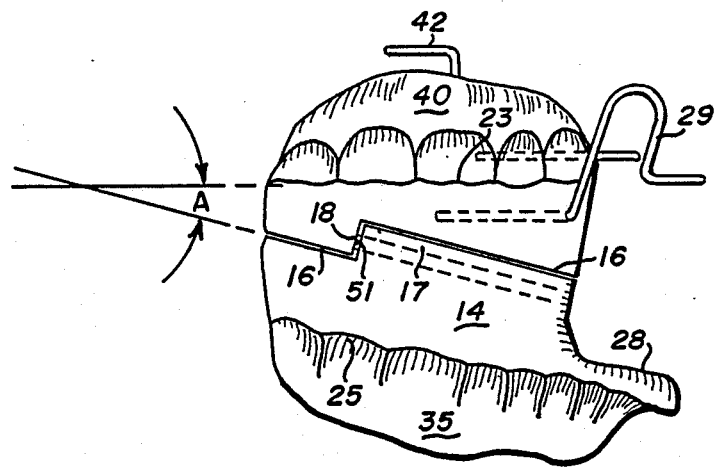
Fig_9b

METHOD AND THERAPEUTIC APPARATUS FOR REDUCING SNORING

FIELD:

The invention relates to a non-surgical, non-invasive therapeutic apparatus and method, more particularly to an adult oral cavity appliance that repositions the mandible in an inferior (open) and anterior (protrusive) position, as compared to the normally closed position of the jaw, in order to improve airway patency for reducing snoring and/or obstructive sleep apnea due to intermittent closures or partial obstructions in the oro pharynx.

BACKGROUND:

Hypersomnia sleep apnea syndrome (HSA), the cessation of breathing for periods in excess of 10 seconds during a one hour sleep period, is a potentially life-threatening disorder, the incidence of which is estimated at over 2.5 million persons in the U.S. Two major types of sleep apnea have been described: (1) obstructive (upper airway), and (2) central. The obstructive type is characterized by a continuation of the respiratory effort during the apneic period, while the central is marked by loss of respiratory effort. A mixed type begins as central but continues as obstructive.

Obstructive sleep apnea is more common in men, 82–95% of cases, and is most often first identified in mid-life with the development of loud snoring and daytime somnolence. It is frequently accompanied by obesity, hypertension, cardiac irregularity and hemodynamic abnormalities. While not all persons who snore have sleep apnea, essentially all people affected with sleep apnea snore. See generally, Weitzman E. D., et al., Quantitative Analysis of Sleep and Sleep Apnea Before and After Tracheostromy in Patients with the Hypersomnia—Sleep Apnea Syndrome, Sleep Vol. 3, No. 314, pp 407–423 (1980).

In severe cases, the apnea incidences (apneic events) may be over 90/hour (see Cartwright et al., at p. 706, below). More moderate cases place those interruptions on the order of 3–50/hour. The cessation of breathing can last for periods of 45 seconds or more, and the patient is frequently aroused, gasping for breath. Death can occur through respiratory coma and/or associated heart problems.

In cases of obesity hypoventilation syndrome, loss of weight has resulted in reduction of snoring and/or apneic episodes. See Harman, E. M. et al., The Effect of Weight Loss on Sleep-Disordered Breathing and Oxygen Desaturation in Morbidly Obese Men, Chest Vol. 82, No. 3, pp 291–294 (Sept. 1982).

When obstructive sleep apnea is of serious proportions, surgery, specifically tracheostomy, may be the treatment of choice. However, patients often reject this choice as permanent tracheoctomy results in physical disability and psychological problems. See generally, Conway, W. A. et al., Adverse Effects of Tracheostomy for Sleep Apnea, JAMA Vol. 246, No. 4, pp 347–350 (July 24/31, 1981).

Another surgical approach is to reduce/remove deformities, or enlarge the airway. This approach includes uvulopalatopharygoplasty (UPPP), which is a removal of a portion of the soft palate to prevent closure of the airway in the pharynx region. See generally, Fujita, S., et al., Surgical Correction of Anatomic Abnormalities in Obstructive Sleep Apnea Syndrome: uvulopalatopharygoplasty, Otolaryngol Head Neck Surg., Vol. 89, pp 923–934 (Nov/Dec 1981).

A non-surgical approach involves applying positive airway pressure by use of low pressure mask. Continuous positive airway pressure (CPAP) provides a pneumatic splint for the nasopharyngeal airway. A variation is EPAP, expiratory positive airway pressure by a similar apparatus. See generally, Sullivan, C. E. et al., Reversal of Obstructive Sleep Apnea by Continuous Positive Airway Pressure Applied Through the Nares, The Lancet, Apr. 18, 1981, pp 862–865, and Mahadevia, A. K. et al., Effects of Expiratory Positive Airway Pressure on Sleep-Induced Respiratory Abnormalities in Patients with Hypersomnia-Sleep Apnea Syndrome, Am Rev Respir Dis 1983, Vol 128, pp 708–711.

Another non-surgical approach to reducing sleep apnea or stopping snoring has been the use of various types of oral cavity appliances. Several oral cavity appliances are the subject of U.S. patents. Strickland U.S. Pat. No. 3,434,470 is directed to a snore inhibiting device comprising a maxillary plate to decrease the air flow in the U-shaped spaced defined by the upper teeth. It has a resilient channel (U-shaped in cross section) which releasably grips the upper teeth, and a pair of overlapping moveable plate sections bridging the space between the left and right side teeth so that one size fits all. This device, in closing the oral cavity airway, functions the opposite of the instant invention. Further, it does not reposition the mandible.

Tepper U.S. Pat. No. 3,277,892 is directed to an apparatus for correcting protruding tongue problems which lead to malocclusion, speech defects (lisping) and incorrect swallowing. It is not directed to snore or apnea reduction. It employs a full palate retainer of the Hawley type and means for imparting an electrical shock when the tip of the patient's tongue is thrust forward to within 2 mm of the lingual surface of the upper incisors. Gibbons U.S. Pat. No. 2,844,142 is directed to a tongue retainer device which prevents an unconscious or semi-conscious person from swallowing the tongue blocking the trachea, or may be used during dental operations. The device comprises a pair of concentric rings, the inner suspended from the outer by a flexible strand. The large loop is placed over the jaw and the tongue is inserted in the smaller inner loop. The device does not reposition the mandible. Interestingly, Gibbons comments that horses have difficulty breathing when they run as the excitement and exertion causes swelling of the tongue, which results in the tongue falling backwardly into the throat. The device is said to improve breathing capacity of horses.

Ronn U.S. Pat. No. 1,401,646 is directed to a saliva ejector comprising a pair of bent perforated tubes which straddle the teeth. It is unrelated to snore reduction. Williams U.S. Pat. No. 1,498,219 is directed to a mouth prop for holding the mouth open and supporting cotton rolls during filling the teeth. It comprises a metal frame with a top plate spanning the palatal arch which is connected at the sides by a U-shaped upright frame. The bottom of the U-frame is connected to a loop that straddles the mandibular dentition. It is silent on how far open the jaw is forced, and does not appear to provide for anterior repositioning. It is silent on use as a snore-reducing device.

In a letter to The New England Journal of Medicine, entitled "Treatment of Obstructive Sleep Apnea with a Nocturnal Airway—Patency Appliance," Vol. 313, No.

6, Aug. 8, 1985, pp 386-387, Soll, B. A. and George, P. T. describe their work of modifying an "activator", a variant of the orthodontic appliance developed in 1902 by Pierre Robin for treatment of severe obstructive sleep apnea. They reference the Robin device to Salzmen, J. A., Practice of Orthodontics, Philadelphia J. B. Lippincott, 1966, but do not describe further its structure or function.

The Soll-George device can be described as an acrylic plastic retainer-like appliance which is placed between the teeth. I is molded so that all of the teeth fit into individual indentations. That is, the device apparently extends from the incisors in the front all the way around to the molars in the rear, both upper and lowers. Four clasps and a double maxillary arch wire serve to retain the device in position. While the NEJM text is silent, it appears from the photograph that the appliance substantially blocks the opening between the teeth with the exception of some small holes. The oral cavity air passage is substantially closed in an apparent attempt to insure that breathing occurs through the nasal passage rather than the mouth. The jaw is positioned somewhat opened with the lower jaw protruding forward. The amount of opening, as measured from the symphysis, is 9 millimeters inferior and 6 millimeters anteriorly, as compared to the normal closed position. Only one case was reported, with the apnea index (the number of apnea episodes per hour) dropping from 79 to 5.3.

Still another device is the TRD, an acronym for Tongue Retaining Device, described by Cartwright, R. D. et al. in The Effect of a Non-Surgical Treatment for Obstructive Sleep Apnea, JAMA Vol. 248, No. 6, pp 705-709, Aug. 13, 1982. This device is a soft copolymer plastic spacer, similar to a boxer or football player's mouthpiece, which holds the jaw in an open position. Its critical feature is use of a "lingual compartment", which is a large bubble protruding forwardly between the teeth, which receives the tongue. Apparently the tongue is retained in the bubble by negative pressure caused by surface tension. This device is worn at night and is reported to cut the apneic index in half, from about 36 to 18 episodes/hour. The TRD causes the patient's mouth to be open with the tongue sticking out. The bubble serves to retain the tongue in the extended position by negative pressure. There is no patency to the oral airway, i.e., the patient cannot breath through the mouth, the TRD completely closing the mouth opening thus forcing breathing through the nasal passages.

The "Bionator" is an appliance for quite a different purpose. This device is an appliance or retainer which causes the mouth to be open for the purpose of permitting the head of the condyle process to grow. In cases of juvenile jaw deformity or immaturity, the neck portion of the condyle at the distal end of the mandible is underdeveloped. With the lower jaw slightly opened, the growth of the mandibular process is stimulated through the application of tension. This juvenile bone corrective device is to be worn as much as possible, both day and night.

One of the disadvantages of the above-described types of appliances is that they can be quite uncomfortable. Muscle strain and the unnatural position causes pain and/or discomfort in the joint and tongue. The design of the Soll/George and TRD appliances does not permit unstrictured open mouth breathing. In addition, devices such as the TRD and CPAP/EPAP masks are cosmetically and psychologically disagreeable, and not condusive to shared sleeping arrangements.

Since the AMA estimates there are some 30 million Americans who snore and 2.5 million who have sleep apnea syndrome, there is still a great need for a simple device which reduces snoring and related apneic episodes, yet is comfortable to wear on a long-term basis, is cosmetically and psychologically acceptable, and provides for relatively full patency of the mouth airway (through the mouth breathing). This invention is directed toward solving those problems.

THE INVENTION

Objects:

It is among the objects of this invention to provide a non-surgical, non-invasive therapeutic appliance, when worn at night by an adult patient, that reduces snoring and/or sleep apnea due to intermittent closures or partial obstructions in the oro pharynx.

It is another object of this invention to provide an improved anti-snoring appliance which also tends to reduce sleep apnea incidences.

It is another object of this invention to provide an adult oral cavity appliance which improves the patency of the oro pharynx airway, yet is comfortable for long-term wear without causing undue jaw muscle strain, or temporal mandibular joint pain or discomfort, and is not cosmetically objectionable or psychologically disturbing.

It is another object of this invention to provide a sleep and nocturnal obstructive apnea reducing appliance which is characterized by a fully opened mouth airway so that the patient may breath through the mouth, or through either or both the mouth and the nasal passages It is another object of this invention to provide an adult oral cavity therapeutic appliance that repositions the mandible in a critical inferior (open) and anterior (protrusive) position to improve the patency of the oro pharynx airway, yet which positioning is relatively comfortable on a long-term basis.

Still other objects of this invention will become evident from the description and drawings.

SUMMARY:

The invention comprises a non-surgical, non-invasive therapeutic apparatus and method, comprising an adult oral cavity appliance that improves airway patency for correcting snoring and/or sleep apnea due to intermittent closures or partial obstructions occurring in the oro pharynx. The appliance is insertable in, and removable from the mouth by the patient, and is used only during sleep periods. It repositions the mandible in an inferior (open) and anterior (protrusive) position as compared to the normal closed position of the jaw, typically, on the order of 10 to 20 millimeters inferior, and 3 to 10 millimeters (preferably 3 to 6 millimeters) anterior.

The appliance of this invention comprises a rigid, preferably acrylic, generally V-shaped wedge molded to the entire mandibular dentition and a portion of the maxillary dentition. The appliance of this invention is completely open in the front, at least from canine to canine, and preferably open at the top (across the palatal arch). The mandibular incisal edge is embedded from cuspid to cuspid, with a lip extending about 1 to 2 millimeters over the labial surface of the mandibular incisors. Neither the bicuspids or molars are embedded. The appliance is open on the sides too, that is, it does not embed or cover the buccal surfaces of these teeth. The occlusal surfaces and lingual cusps of all mandibular teeth are embedded, with the appliance extending over the lingual surfaces and extending downwardly into the lingual vestibule. The appliance contacts and covers only the occlusal surfaces and palatal cusps of the maxillary bicuspids and molars. It covers the palatal surfaces of the same teeth and extends onto the palate. It is preferred that the palate is not covered. Crosswise palatal stiffening is provided by a heavy dental wire, e.g., "Elgiloy" brand stainless steel, rather than an acrylic arch. The lack of palatal coverage permits the prosthesis to be less bulky, thus providing space for the tongue. No facial surfaces of the teeth are covered by the appliance except for the mandibular incisors.

The tongue rests more or less in its normal position, and is not thrust forward between the lips as in the TRD device. A clip or clasp may be provided at the first maxillary molars to provide snap-fit retention. The molar clasps are positioned above the height of contour so that they are approximately 0.01" inwardly of the exterior profile, with the vertical legs passing in or adjacent the embrasures. A labial arch wire which fits over and extends between the maxillary canines is provided to prevent splaying of the teeth. A cingulum arch wire is provided to prevent eruption of the maxillary incisors.

Within the ranges indicated, the amount of inferior and anterior positioning may be adjusted so that there is no discomfort in the muscles or the temporal mandibular joint, e.g., as may be caused by cramping of the masseter muscle, the lateral and medial pterygoid muscles, or the pterygo-palatine muscle. The amount of anterior extension and inferior position of the jaw must be sufficient however to significantly reduce and substantially eliminate snoring.

The appliance is to be worn by adults during sleep periods. In contrast, a Bionator is to stimulate skeletal long bone growth in children. Typically, the differential growth rate of skeletal bones as compared to cranial bones can result in mandibular deformity. The Bionator provides tension on the condyle area which stimulates growth of the mandibular skeletal bone to catch up to the cranial growth. The Bionator positions the jaw in a barely open position, with only slight protrusion, on the order of 1 to 2 millimeters.

The Soll/George appliance appears to encapsulate both the maxillary and mandibular teeth, including the maxillary incisors. It is not known whether the appliance extends into the lingual vestibule. The appliance employs a modified labial wire with a parallel cross piece being positioned above the maxillary gum line. In addition, the Soll/George appliance is essentially closed in the front, with only a few small holes which are, practically speaking, inadequate as any form of airway. The Soll/George appliance employs both upper and lower circumferential clasps for retention. In addition, the reported inferior position of the Soll/George appliance is small, being typically less than 9 millimeters as measured from the symphisis, while the anterior protrusion is reported as 6 millimeters. The mandible appears to be positioned more nearly parallel to the maxilla, rather than being open in a pronounced V as in the appliance of this invention.

It should be understood that by maxillary and/or mandibular "dentition" is meant not only natural dentition but also any prosthesis, be it a bridge, partial or full denture or implant.

DRAWINGS:

The detailed description has reference to the drawings in which:

FIG. 1 is a partial schematic side elevation section view with the mouth closed showing a snoring and apnea causing airway obstruction in the oro pharnyx region;

FIG. 2 is a similar view showing the appliance of this invention in place, positioning the jaw in an inferior and anterior position with the result that the oro pharnyx airway is now open;

FIG. 3 is a three-quarter perspective from above and to the right side of the appliance of this invention;

FIG. 4 is a right side elevation view of the appliance of this invention;

FIG. 5 is a front elevation view;

FIG. 6 is a rear elevation view;

FIG. 7 is a bottom plan view;

FIG. 8 is a top plan view; and

FIGS. 9a and 9b are a related pair of side elevation views, FIG. b being in section, of another embodiment of the invention having means for adjustment of the anterior and inferior position, with FIG. 9a showing a first, mid-point position, and FIG. 9b showing a second position adjusted to be retracted (less open).

DETAILED DESCRIPTION OF THE BEST MODE OF CARRYING OUT THE INVENTION:

The following detailed description illustrates the invention by way of example, not by way of limitation of the principles of the invention. This description will clearly enable one skilled in the art to make and use the invention, and describes several embodiments, variations, alternatives and uses of the invention, including what I presently believe is the best mode of carrying out the invention.

FIG. 1 is a partial schematic side elevation section view somewhat in the nature of an outline tracing of an x-ray of a patient 1 who is experiencing a snoring problem and/or sleep apnea due to an intermittent closure or partial obstruction in the airway 2 of the oro pharyngeal region 3. That region is distinct from the region of the nasal pharnyx 4. This partial or complete, intermittent obstruction or closure can occur, for example during sleep periods when the distal (rear) portion of the tongue 5 upon relaxation slides backwardly, narrowing the airway as shown in the circled region 12. In addition, during sleep and when the person is in a prone position, the oral cavity tissues can relax, or collapse sufficiently to cause intermittent closure. As seen in FIG. 1, the rear dorsal surface of the tongue 5 may extend sufficiently back to partially or fully close the airway 2. In addition, it may touch the soft palate 6.

This invention is not directed to resolving problems of closure which may occur in the nasal pharnyx region 4. Those problems may be approached through surgery, for example by uvulopalatopharyngoplasty, or other procedures. By way of information, the Bionator would affect growth of the ramus just below condyle 7 of the mandible 8. In FIGS. 1 and 2, item 9 is the maxilla, 10 is the nasal cavity and 11 is the temporal bone.

FIG. 2 is a partial schematic side elevation view showing the appliance of this invention 20 in place between the maxillary and mandibular dentition. Note that the dorsal surface of the tongue has now been moved forwardly to the position 15 as compared to the original position 5 shown in phantom. The result is that the oro pharynx airway 2 is now substantially fully open. By comparing FIGS. 1 and 2, it can be seen that the mandible (lower jaw) is open (inferior), and moved anteriorly (protrusively) as compared to the closed position.

The appliance of this invention 20 is shown in detail in FIGS. 3 through 9. The appliance is preferably made of a heat-cureable plastic, such as dental acrylic, having dental wires for stabilization of the appliance itself and the teeth. The appliance comprises a pair of generally V-shaped body portions 21, 22 which receivingly engage portions of the maxillary dentition along molded surfaces 23 (right side) and 24 (left side), and mandibular dentition along right side surface 25, incisal surface 26 and left side surface 27. As can be seen in the figures, particularly FIGS. 3 and 4, there is a pronounced V-shaped spacer member 21 defined between the right side maxillary dentition surface 23 and the right side mandibular dentition 25. The same V-shaped spacer member 22 is present on the left side between the corresponding maxillary surface 24 and mandibular surface 27. The two side pieces are joined in the front by a mandibular acrylic bridge 28 and upper dental wires, of which wire 29 is a maxillary labial arch wire and 30 is the cingulum arch wire. The labial arch wire fits over and extends between the maxillary canines to prevent splaying of the incisors. The cingulum arch wire prevents eruption of the maxillary incisors.

A continuous semicircular lingual flange 35 extends downwardly from the spacer members 21, 22 and the mandibular bridge 28. As can be best seen in FIGS. 3 through 7, this lingual flange extends downwardly over the lingual surfaces of the mandibular teeth into the lingual vestibule. The appliance is molded so that the lingual cusps of all mandibular teeth are embedded in the spacers 21, 22. The appliance is smoothly fared on the interior/upwardly facing surface to form the lingual flange. The lingual surface molding 36 is best shown in FIGS. 4 and 7.

As best in seen FIGS. 3–5 and 7, the mandibular incisal edge is embedded from cuspid to cuspid with a mandibular incisal lip 37 extending about 1 to 2 millimeters over the buccal surface of the mandibular incisors. The resulting notch 38 receivingly engages the mandibular incisors to cause the mandible (lower jaw) 8 to protrude forwardly as best shown in FIG. 2. As seen in FIG. 7 in phantom, where the patient still has wisdom teeth 31, 32, the appliance can be extended rearwardly to contact their lingual cusps. However, it is preferred to terminate the appliance short of the wisdom teeth as shown in solid lines.

The appliance contacts and covers only the palatal cusps of the maxillary bicuspids and molars (but preferably need not extend to the wisdom teeth) as shown by the respective maxillary dentition surfaces 23 and 24. The appliance has a pair of upwardly extending palatal surface flanges 40 (right side), 41 (left side). These flanges extend upwardly to cover the palatal surfaces of the maxillary bicuspids and molars, and then upwardly and inwardly onto the palate. It is likewise fared smoothly into the V-shaped spacer members 21, 22. It is preferred that the entire palate is not covered, as best shown in FIGS. 3, 5, 6 and 8. As shown in these Figures, crosswise palatal stiffening is provided by heavy dental wire 42 rather than a full arch of acrylic material. Any suitable type of dental wire may be employed for the palatal stiffener 42. The absence of extensive or thick palatal flanges and complete palatal arch permits the appliance to provide space for the tongue and an airway of sufficient capacity to breathe. The tongue rests more or less in a normal position and is not thrust forward between the patient's lips as best seen in FIG. 2.

While FIG. 2 shows the patient's mouth open, it should be understood that most patients can close their lips with the appliance in proper position. However, as best seen in FIGS. 3 through 6, the appliance of this invention is completely open in front from canine to canine, thus permitting a sufficiently large aperture for breathing should the patient wish to breathe through his/her mouth. Since a substantial portion of the palatal and lingual surfaces are covered, and the side walls of the cheeks are shielded by the spacers 21, 22, the patient does not have excessively dry mouth during sleep periods when the patient experiences open mouth breathing.

The appliance is also open at the sides in the sense that it does not embed or cover the buccal surfaces of teeth. Neither the mandibular bicuspids nor molars are embedded. The same is true for the maxillary bicuspids and molars. A pair of clips or clasps 45, 46 are provided, preferably at the first maxillary molar to provide snap-fit retention. This is best seen in FIGS. 3 through 6. The molar clasps are positioned above the height of contour of the molars so that they are approximately 0.01 inch inwardly of the exterior profile. The verticle legs of the clasps pass in or adjacent to the embrasures between the teeth. As with the palatal, labial, and cingulum arch wires, the molar clasps may be of any suitable dental stainless steel, such as "Elgiloy" brand stainless steel.

The appliance of this invention is easily insertable in the mouth by the patient. It is used only during sleep periods and removed at the end of that time. The appliance repositions the mandible in an inferior (open) and anterior (protrusive) position as compared to the normal closed position of the jaw. Typically, the appliance will position the lower jaw from 10 to 20 millimeters open (inferior), and from 3 to 10 millimeters, preferably 3 to 6 millimeters protrusive (anteriorly) of the closed position. Within the ranges indicated, the amount of inferior and anterior positioning may be adjusted so that the patient does not experience discomfort. Typically, discomfort may occur in the temporal mandibular joint or in the jaw muscles such as the masseter muscle, the lateral and medial pterygoid muscles, or the pterygopalatine muscle.

In practice, I prefer to start with a portion of 20 millimeters inferior (open), and then close slightly. I also begin with the maximum point of auto-protrusion (the farthest the patient is capable of anterior extension of the jaw by him/herself) without hyperextension of the temporal mandibular joint (TMJ). If external tension is applied, the TMJ can be hyperextended resulting in extreme discomfort and/or pain in the TMJ and the above-identified muscles if maintained in that position for any length of time.

Once this position has been identified, then the patient is tested for function, i.e., can the patient snore? I have discovered that very slight differences in position, on the order of plus/minus 0.5 millimeters in terms of inferior and interior positioning can radically affect, that is eliminate, the snoring. I then test to see if the non-snoring functional position is comfortable on a long-term basis. The patient's jaw is maintained in the initial no-snore inferior/anterior position for an extended period, on the order of 10 to 30 minutes. Cramping should occur well within that period. If cramping is evident, then the anterior position is reduced approximately one-half millimeter at a time until comfortable to prevent fatigue or strain over the length of a sleeping period. In practice, I have found that the 6 millimeter extension is extremely far forward and that protrusion on the order of 3 to 5½ millimeters is the preferred position for most patients. I have also discovered that a 9 millimeter opening is almost universally ineffective, in that the patient should be open in the rang of 10 to 20 millimeters.

Once the above procedure has been followed to determine the operative snore reduction position, an appropriate mold is taken of the maxillary dentition, and of the mandibular dentition. These molds are then mounted in the recorded position for formation of the appliance template. The appliance is then cast of acrylic in a conventional manner employing conventional dental acrylic. The appropriate labial, cingulum and palatal arch wires and the molar clasps are embedded in the appliance during the casting procedure.

SPECIFIC EXAMPLES:

Case I

A 55 year old male patient, height 5'10", weight 188 lbs., sought treatment for a snoring problem associated with a diagnosed obstructive sleep apnea condition. His wife had observed the loud bothersome snoring and frequent interruptions in breathing. The patient related that he awakened numerous times each night while struggling and gasping for air. He was tired, run down and had multiple episodes of daytime somnolence.

The patient was evaluated with the following results: The patient is overweight and drinks heavily on occasion. The patient is retromandibular. The tonsils and adenoids have been removed. The airway is constricted due to a long, broad and flaccid soft palate and a large dense tongue.

The patient was fitted with the appliance of this invention following the procedures outlines above. He wears the appliance every night, and it has eliminated all the snoring and associated symptoms of obstructive apnea. His wife now indicates his problem no longer exists. The patient states that the device has improved the quality of his sleep and he no longer feels drowsy after a full night's sleep.

Case II

A 47 year old male patient, a professional fireman, height 5'7", weight 177 lbs., sought treatment for a snoring problem that was associated with a diagnosed obstructive sleep apnea condition. His wife and co-workers in the fire station had all commented on his extremely loud and bothersome snoring. They had observed apnea episodes lasting as long as 45 seconds. The patient was also bothered with some daytime sleepiness. Sleep lab results indicated seventeen respiratory abnormalties per sleep hour. Each event would typically last 35 seconds and the longest events lasted 46 seconds. The patient had previously sought treatment with a surgical operation (nasal septoplasty and uvulopalatopharyngoplasty) to cure the problems, but the operations did not relieve the condition.

The patient was evaluated with the following results: The patient smoked one pack of cigarettes per day for over 25 years. Patient is overweight. The tonsils and adenoids have been removed. The removal of the uvula and surgical correction of the soft palate, pharynx and nasal septum were noted. The patient is retromandibular with a large massive tongue. These conditions combined to create an airway obstruction that occluded during sleep and produced the snoring.

The patient was fitted with the appliance of this invention following the procedures outlined above. The results were immediate and very positive. His wife and co-workers all reported no snoring. The patient indicates he sleeps better and experiences none of the previous sleep apnea symptoms. He states it is very comfortable to wear with no side effects. He has on occasion even rushed to the scene of an emergency to find himself still wearing the device after he has arrived.

Approximately 50 additional cases have been prepared with similar results from use of the appliance of this invention. Indeed, the appliance is equally effective in reducing snoring in cases where the patient does not have all his natural teeth. For example, the appliance has been effective in cases of both full and partial dentures, the appliance being molded to and worn over the dentures. The cases have included: males and females, all adult ages (25–79), a full variety of physical types and body weights, and those who have not had success in stopping snoring with uvulopalatopharygoplasty. Two cases were formerly on CPAP apparatus, and are now using the appliance as an alternative, particularly when they travel. In the case of dentures the dimensions may be reduced and the labial arch wire may be eliminated.

FIGS. 9a and 9b show an alternate embodiment of the invention which is adapted for simultaneous adjustment, of both the inferior and anterior position of the appliance after fitting to the patients' dentition.

Each of the wedge-shaped spacers 21, 22 are formed in two pieces, upper portion 13, and lower portion 14, or the spacers are cut along line 16, to form step 17 in lower portion 14 and shoulder 18 in upper portion 13. As shown in the Figures, the line of separation 16 is canted at an angle of from about 3 degrees to 30 degrees down from the horizontal. This angle is identified in FIG. 9a with the letter "A", and is defined as the included angle between a generally horizontal line defined by the maxillary dentition and a rearward extension of the cut or line of separation 16 between the upper and lower portions of the spacer. I presently prefer an angle of about 10–15 degrees.

Alternatively, where the initial settings are 15 mm inferior (open) and 3 mm anterior (protrusive), the angle may be set within that range so the same anterior (protrusive)/inferior (open) ratio of 1/5 is kept throughout the range of adjustments.

A threaded adjustment rod 50, having an unthreaded end portion 51 is received in threaded bore 52 in the lower step portion 14. Access to hex recess 53 is obtained through hole 54. To adjust the position a mating hex-ended screwdriver or allen-type wrench is inserted in the recess and the screw turned to increase or decrease the open/protrusive position. The end 55 of the rod 50 bears on a shoulder 18.

FIG. 9a shows this alternative embodiment in its normal, initial or start position, which is approximately the mid-point of the 10–20 mm inferior and 3–6 mm anterior range. FIG. 9b shows the appliance adjusted to a more closed (retracted) position. Turning the screw the other way will open the appliance more. The screw 50 may be metal or plastic.

It should be understood that various modifications within the scope of this invention can be made by one of ordinary skill in the art without departing from the spirit thereof. For example, the cut 16 may be keyed to prevent lateral movements of the parts 13 and 14 with respect to each other. In the FIG. 9 embodiment the jaw muscles provide pressure (from right to left in the figures) holding the end 55 against the shoulder 18. However, the two parts 13, and 14 may be spring-biased together, e.g. with orthodontic type rubber bands on appropriate hooks, so that the adjustment works against that pressure. In cases where the patient has lost some or all of his/her teeth, the spacer may be molded to either the replacement prosthesis (implant, bridge or partial or full denture) or the tissue covering the alveolar process of either or both the mandible and/or the maxilla. I therefore wish my invention to be defined by the scope of the appended claims as the prior art will permit, and in view of the specification if need be.

I claim:

1. A therapeutic appliance for reducing adult oropharyngeal occlusion-induced snoring and obstructive sleep apnea during sleep periods, adapted to fit between the maxillary and mandibular dentition in the adult oral cavity, comprising in operative combination:
    (a) a pair of generally V-shaped spacer members, each having a truncated apex and a base spaced from said apex, said spacers being adapted to be positioned in an adult oral cavity between the maxillary and mandibular dentition with the apex toward the posterior of the dental arches;
    (b) said V-shaped spacers being disposed in a spaced-apart, side-by-side relationship removably insertable and matingly engaging at least one of the maxillary bicuspids and molars and the alveolar process of the maxilla and at least one of the mandibular dentition of an adult patient and the alveolar process of the mandible;
    (c) said V-shaped spacers being oriented with said base of each adjacent the bicuspids and the apex of each adjacent the molars of the dental arch;
    (d) an arcuate member bridging the space between the base of said spacers and extending to cover the lingual surfaces of the mandibular incisors;
    (e) said arcuate member having a lip portion extending over a portion of the labial surface of the mandibular incisors, the incisors being matingly embedded in said lip portion;
    (f) a first pair of flanges, each extending from said V-shaped spacers along the lingual surface of the mandible; and
    (g) a second pair of flanges, each extending from said V-shaped spacers along the palatal surface of at least one of said maxillary bicuspids and molars, and having a forward margin;
    (h) an arcuate cingulum wire disposed to bridgingly join the forward margins of said second pair of flanges;
    (i) a molar clasp disposed at the first maxillary molars, left and right;
    (j) said palatal flanges are connected by at least one means for lateral stiffening;
    (k) said spacers and said arcuate bridge member being adapted;
        (i) to provide a substantial vertical distance between the maxillary and mandibular dentition to create an open mouth position;
        (ii) to maintain the mandible in said open mouth position within the range of from about 10 to about 20 mm inferior and from about 3 to about 6 mm anterior as compared to the normal closed position of the mandible to create an open oral airway to permit functional breathing through the oral cavity; and
        (iii) to cause both anterior and inferior repositioning of the tongue to reduce incidence of tongue-induced obstructive sleep apnea and snoring associated therewith.

2. An appliance as in claim 1 wherein the base of at least one spacer extends to engage at least one wisdom tooth.

3. An appliance as in claim 2 wherein only the occlusal surfaces and lingual cusps of the mandibular teeth are embedded in said spacers, and only the occlusal surfaces and palatal cusps of the maxillary bicuspids and molars are embedded in said spacer.

4. An appliance as in claim 3 which includes means for adjusting at least one of the anterior and inferior positions disposed in each of said spacers, said spacers being divided into an upper and a lower segment along a longitudinal line inclined at an angle of from about 3 to 30 degrees down from the horizontal, said angle being defined as the included angle between a generally horizontal line defined by the maxillary dentition and a rearward extension of the division between said spacers.

5. An appliance as in claim 2 which includes means for adjusting at least one of the anterior and inferior positions disposed in each of said spacers, said spacers being divided into an upper and a lower segment along a longitudinal line inclined at an angle of from about 3 to 30 degrees down from the horizontal, said angle being defined as the included angle between a generally horizontal line defined by the maxillary dentition and a rearward extension of the division between said spacers.

6. An appliance as in claim 1 which includes means for adjusting at least one of the anterior and inferior positions.

7. An appliance as in claim 6 wherein only the occlusal surfaces and lingual cusps of the mandibular teeth are embedded in said spacers, and only the occlusal surfaces and palatal cusps of the maxillary bicuspids and molars are embedded in said spacer.

8. An appliance as in claim 7 wherein the base of at least one spacer extends to engage at least one wisdom tooth.

9. An appliance as in claim 6 wherein said adjusting means is disposed in each of said spacers.

10. An appliance as in claim 9 wherein only the occlusal surfaces and lingual cusps of the mandibular teeth are embedded in said spacer, and only the occlusal surfaces and palatal cusps of the maxillary bicuspids and molars are embedded in said spacer.

11. An appliance as in claim 9 wherein said spacers are divided into an upper and a lower segment along a longitudinal line inclined at an angle of from about 3 to 30 degrees down from the horizontal, said angle being defined as the included angle between a generally horizontal line defined by the maxillary dentition and a rearward extension of the division between said spacers.

12. An appliance as in claim 11 wherein only the occlusal surfaces and lingual cusps of the mandibular teeth are embedded in said spacer, and only the occlusal surfaces and palatal cusps of the maxillary bicuspids and molars are embedded in said spacer.

* * * * *